United States Patent [19]
Cowsert et al.

[11] Patent Number: 5,821,050
[45] Date of Patent: Oct. 13, 1998

[54] DRUG SCREENING ASSAY FOR ANTIVIRAL ACTIVITY AGAINST PAPILLOMAVIRUS

[75] Inventors: Lex M. Cowsert, Carlsbad, Calif.; Paul R. Clark, Tucson, Ariz.

[73] Assignee: Isis Pharmaceuticals, Inc., Carlsbad, Calif.

[21] Appl. No.: 678,164

[22] Filed: Jul. 11, 1996

Related U.S. Application Data

[60] Provisional application No. 60/001,157 Jul. 14, 1995.

[51] Int. Cl.$^6$ .............................. C12Q 1/70; C12Q 1/68; A01N 37/18; C12N 15/00
[52] U.S. Cl. ................................ 435/5; 435/6; 435/91.1; 435/91.2; 514/2; 514/44; 935/76; 935/77; 536/23.1; 536/23.72; 536/24.32
[58] Field of Search .................................. 435/6, 5, 91.1, 435/91.2, 235.1, 270, 183; 514/2, 44; 935/1, 33, 76, 77; 536/23.1, 23.72, 24.32

[56] References Cited

U.S. PATENT DOCUMENTS

| | | | |
|---|---|---|---|
| 4,921,805 | 5/1990 | Gebeyehu et al. | 435/270 |
| 5,601,975 | 2/1997 | Bonyhadi et al. | 435/5 |

OTHER PUBLICATIONS

A. M. Del Vecchio et al., "Transient Replication of Human Papillomavirus DNAs," Journal of Virology, vol. 66, No. 10, pp. 5949–5958, Oct. 1992.

W. Brune and M. Durst, "Epithelial Differentiation Fails to Support Replication of Cloned Human Papillomavirus Type 16 DNA in Transfected Keratinocytes," The Journal of Investigative Dermatology, vol. 104, No. 2, pp. 277–281, Feb. 1995.

M. Bossens et al., "In vitro infection of normal human keratinocytes by human papillomavirus type 1 followed by amplification of the viral genome in reconstructed epidermis," Jouranal of General Virology, vol. 73, Part 12, pp. 3269–3273, Dec. 1992.

Bauer et al., "Determinants of Genital Human Papillomavirus Infection in Low–Risk Woment in Portland, Oregon," *Sex. Transm. Dis.*, 1993, 20, 274–278.

Beutner et al., "Epidemiology of Human Papillomavirus Infections," *Dermatol. Clin.* 1991, 9, 211–218.

Chiang et al., "Viral E1 and E2 Proteins Support Replication of Homologous and Heterologous Papillomaviral Origins," *Proc. Natl. Acad. Sci. U.S.A.* 1992, 89, 5799–5803.

Chiang et al., "Control of Human Papillomavirus Type 11 Origin of Replication by the E2 Family of Transcription Regulatory Proteins," *J. Virol.* 1992, 66, 5224–5231.

Cowsert et al., "In Vitro Evaluation of Phosphorthioate Oligonucleotides Targeted to the E2 mRNA of Papillomavirus", *Antimicrob. Agents Chemother.* 1993, 37, 171–177.

Del Vecchio et al., "Transient Replication of Human Papillomavirus DNAs," *J. Virol.* 1992, 66, 5949–5958.

Hirt, B., "Selective Extration of Polyoma DNA from Infected Mouse Cell Cultures," *J. Mol. Biol.* 1967, 26, 365–369.

Schiffman et al., "Epidemiologic Evidence Showing That Human Papillomavirus Infection Causes Most Cervical Intraepithelial Neoplasia," *J. Natl. Cancer Inst.* 1993, 85, 958964.

Ustav and Stenlund, "Transient Replication of BPV–1 Requires Two Viral Polypeptides Endcoded by the E1 and E2 Open Reading Frames," *EMBO J.* 1991, 10, 449–457.

Yang et al., "Activation of BPV–1 Replication in vitrro by the Transcription Factor E2," *Nature* 1991, 353, 628–632.

*Primary Examiner*—Bradley L. Sisson
*Attorney, Agent, or Firm*—Law Offices of Jane Massey Licata

[57] ABSTRACT

A method for screening candidate antiviral drugs by monitoring papillomavirus replication in vitro in the presence of candidate drugs is provided.

3 Claims, 4 Drawing Sheets

DRUG SCREENING ASSAY FOR ANTIVIRAL ACTIVITY AGAINST PAPILLOMAVIRUS

This application claims the benefit under U.S.C. Provisional application Ser. No. 60/001,157 filed on Jul. 4, 1995.

FIELD OF THE INVENTION

This invention relates to an assay for screening candidate drugs for antiviral activity against papillomavirus by monitoring human papillomavirus DNA replication in vitro.

BACKGROUND OF THE INVENTION

Papillomaviruses are known to infect squamous epithelial cells of a wide variety of species. Human papillomavirus (HPV) infection is associated with epithelial neoplasms ranging from benign common warts to invasive carcinoma of the cervix. While HPV can infect many anatomical sites, it is the infection of the anogenital region that is clinically the most important. The HPV types that are associated with anogenital regions are divided into two groups, namely the low-risk HPV group (including HPV-6 and HPV-11) and the high-risk group (including HPV-16 and HPV-18) . The low-risk HPVs are associated with venereal warts or condyloma acuminata, while the high-risk HPVs are associated with intraepithelial neoplastic lesions that can progress to malignancy, most notably cervical carcinoma.

The significance of genital HPV infection is derived from its sexual mode of transmission, near epidemic proportions, Beutner et al., *Dermatol. Clin.* 1991, 9, 211, clear association of certain HPV types with the development of cervical dysplasia, and the progression of dysplasia to cervical cancer, Schiffman et al., *J. Natl. Cancer Inst.* 1993, 85, 958. Because of its sexual mode of transmission, genital HPV infection is particularly prevalent among the young sexually active population. For example, one study [*Oregon Sex. Transm. Dis.* 1993, 20, 274] documented that 46% of women attending a university health center for routine gynecological examination were infected with HPV. The enormity of the problem is underscored by the 1990 CDC estimate of 800,000 new cases of HPV infection diagnosed in the United States.

The goal of current therapeutic approaches to HPV infection is the removal of exophytic warts and the elimination of signs and symptoms of the disease, not eradication of viral DNA. While nearly all genital warts can be eliminated by cryotherapy, electrodesiccation or surgical removal, the recurrence rates are unacceptable. This is likely due to residual virus in adjacent normal tissues.

In general, chemotherapeutic approaches to the control of HPV infection suffer from a lack of specificity. Papillomaviruses do not encode their own DNA polymerase and must therefore rely upon host cellular machinery for replication. This dependence on cellular pathways for replication may explain, in part, the stringent tissue tropism displayed by papillomaviruses. This tight association with cellular pathways and lack of viral polymerases makes it difficult to identify chemotherapeutic agents with appropriate selectivity.

Molecular studies have identified the products of the E1 and E2 open reading frames (ORFs) as essential for viral DNA replication, Chiang et al., *J. Virol.* 1992, 66, 5224; Chiang et al., *Proc. Natl. Acad. Sci. U.S.A.* 1992, 89, 5799; Ustav and Stenlund, *EMBO J.* 1991, 10, 449 and Yang et al., *Nature* 1991, 353, 628. These studies were carried out by providing E1 and E2 in trans and observing replication of reporter plasmids containing an HPV origin of replication (ori) . While these model systems provide an assay system for fine molecular characterization and elucidation of the intermolecular interactions required for viral DNA replication, they do not address replication in the context of the entire viral genome. Thus, these systems cannot identify compounds that do not act directly on E1 or E2, or their interaction with the ori. Recently, autonomous replication of intact HPV-6, HPV-11 and HPV-18 was reported by Del Vecchio et al., *J. Virol.* 1992, 66, 5949. Their study demonstrates that the full-length genomic DNAs of HPV-11 and HPV-18 are able to replicate transiently after transfection into several different squamous cell carcinoma cell lines.

One of the major hindrances to the identification and development of antiviral compounds which are active against HPV is the lack of suitable in vitro models for evaluating compounds with antiviral activity. There exists a need for an assay which can be used as an antiviral drug screening tool. Such an assay system would allow the monitoring of HPV DNA replication in the presence of antiviral agents.

SUMMARY OF THE INVENTION

In accordance with the present invention, a method for screening candidate antiviral drugs by determining their ability to inhibit HPV DNA replication in vitro is provided. HPV DNA replication is monitored in the context of the intact viral genome, under a variety of biological influences and in the presence of antiviral agents. In a preferred embodiment, a method for screening candidate antiviral drugs by monitoring their ability to inhibit HPV-11 DNA replication in vitro is provided.

DETAILED DESCRIPTION OF PREFERRED EMBODIMENTS

Figure 1:
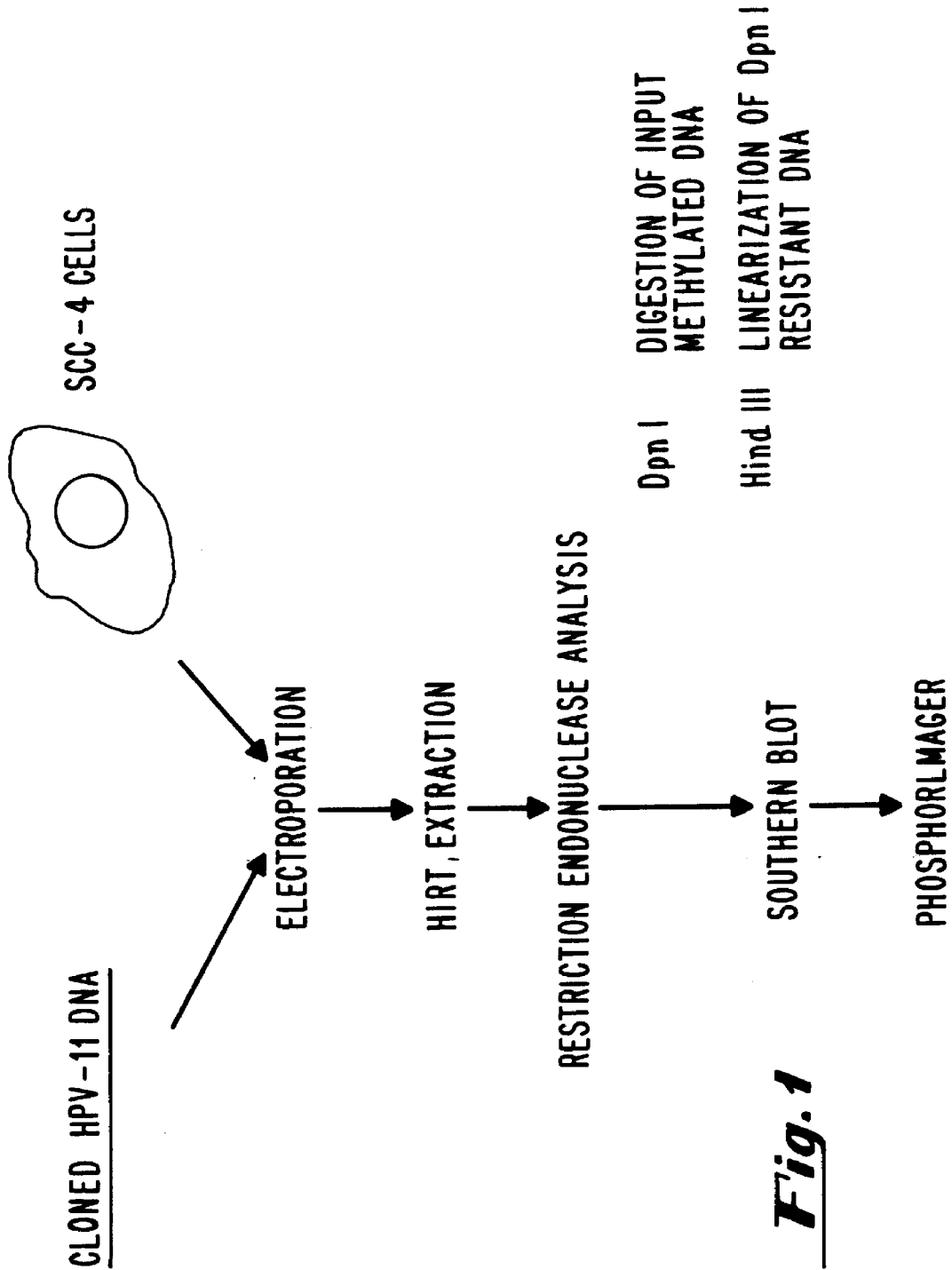
FIG. 1 is a schematic representation of the experimental protocol for the introduction and analysis of HPV-11 DNA in SCC-4 cells.

The present invention provides a model system for screening the effect of antiviral compounds on HPV DNA replication in vitro. This assay is capable of monitoring the effects of such drugs on HPV DNA replication in the context of the intact viral genome, under a variety of biological influences, and in the presence of antiviral agents.

In benign papillomavirus-induced disease, the viral genome is maintained as a low-copy-number episome in the nucleus of basal cells of infected epithelium. As infected cells progress through the differentiation pathway, viral DNA copy number increases, late genes are expressed, viral DNA is encapsidated, and infectious virions are released. It is believed that infection is maintained by the continued presence of low copy viral DNA in basal cells, rather than by reinfection. Therefore, inhibition of viral DNA replication is believed to provide an opportunity for viral clearance from the epithelium.

A major hindrance to the identification and development of antiviral drugs which are active against HPV is the lack of suitable in vitro models for testing the antiviral activity of candidate drugs. It has previously been shown that HPV-11 DNA can autonomously replicate in SCC-4 cells. This HPV-11 DNA replication can be measured and quantitated. The present invention exploits these features to provide an assay which can be used to screen potential antiviral drugs for their ability to inhibit papillomavirus DNA replication.

According to the present invention, SCC-4 cells are transfected by electroporation with cloned HPV-11 DNA. Following transfection, the cells are allowed to grow in the presence and absence of a candidate drug. Low molecular weight DNA is then extracted from the cells according to the method of Hirt, *J. Mol. Biol.* 1967, 26, 365. The extracted DNA is digested with DpnI so that replicated (non-methylated) viral DNA may be distinguished from input (methylated) viral DNA. DNA which has replicated in eukaryotic cells is not methylated and is resistant to DpnI digestion, while input DNA (replicated in *E. coli*) is methylated on adenine residues and is sensitive to DpnI digestion. Input DNA is digested using DpnI, and DpnI-resistant DNA is linearized with HindIII. The DNAs are separated and analyzed by Southern blotting, and visualized by autoradiography.

The antiviral effect of Afovirsen (ISIS 2105), a 20-mer phosphorothioate oligonucleotide, was determined by transfecting SCC-4 cells with HPV-11 DNA by electroporation. The cells were then treated with Afovirsen formulated in Lipofectin™ (GIBCO-BRL, Gaithersburg, Md.) for 4 hours. Afovirsen was then aspirated and standard growth medium was added. The cells were harvested at 72 hours and low molecular weight DNA was extracted. The extracted DNA was digested with DpnI, separated and analyzed by Southern blotting, and visualized by autoradiography. Decreased HPV-11 replication in the presence of a potential drug as compared to replication in the absence of the drug indicates the antiviral activity of the drug. Afovirsen exhibited an apparent $IC_{50}$ of 70 nM in the assay of the present invention.

α-Interferon and 5-fluorouracil (5-FU) have been used in the clinic for the treatment of papillomavirus-associated disease, and have demonstrated only marginal efficacy. In the assay of the present invention, both failed to show convincing antiviral activity. 5-FU failed to inhibit HPV DNA replication in a dose-dependent manner. Furthermore, the only dose that was inhibitory to HPV DNA replication simultaneously induced significant toxicity. α-Interferon induced a general reduction in HPV DNA replication, but failed to produce a dose response over a wide range of concentrations. These results suggest that the activity observed in vivo for 5-FU and α-interferon may be due to a non-specific mechanism such as antiproliferative activity, local toxicity, or immunostimulation.

Antiviral agents such as ribavirin, acyclovir and ganciclovir also failed to show convincing antiviral activity in the assay of the present invention, while sodium butyrate and bromodeoxyuridine exhibited significant antiviral activity and inhibited HPV-11 DNA replication at subtoxic doses.

The present invention represents the first in vitro assay system available to screen potential antiviral drugs for activity against HPV. Determination of the antiviral activity of Afovirsen demonstrates the usefulness of the present invention. When tested in the assay system of the present invention, Afovirsen was found to be a potent inhibitor of HPV-11 DNA replication. This compound is currently in late phase clinical trials. Other compounds which have shown marginal activity in the clinic, such as 5-FU and α-interferon, showed no selective antiviral activity in the assay of the present invention.

The following examples illustrate the present invention and are not intended to limit the same.

EXAMPLES

Example 1
Cell Culture

The general experimental strategy is shown in FIG. 1. SCC-4 cells (ATCC) were grown and maintained under 5% $CO_2$ in a basal medium consisting of 1:1 DMEM/Ham's F-12 (Life Technologies, Gaithersburg, Md.) supplemented with 10% heat-inactivated fetal bovine serum (FBS, Hyclone, Logan UT). Post-electroporation medium consisted of DMEM/Ham's F-12 (1:1), 10% FBS, 100 µ/mL penicillin-streptomycin, and 0.4 µg/mL hydrocortisone (Sigma, St. Louis, Mo.). All replication and chemotherapeutic studies were conducted in post-electroporation medium.

Example 2
DNA Preparation

Cloned HPV-11 DNA [Cowsert et al., *Antimicrob. Agents Chemother.* 1993, 37, 171] PUC19 (Life Technologies, Gaithersburg, Md.) and pSV2neo DNA (Clontech, Palo Alto, Calif.) were prepared using standard amplification and purification techniques. Prior to electroporation, HPV-11 DNA was digested with BamHI. pUC DNA was linearized with BamHI. Digested DNAs were purified by phenol/chloroform extraction, precipitated in ethanol, and quantitated by spectrophotometry. Stock DNA solutions (250 µg/mL) were prepared in water and stored frozen until use. All DNAs were visualized on ethidium bromide stained agarose gels to ensure proper digestion.

Example 3
Electroporation

SCC-4 cells were trypsinized, collected and centrifuged using standard cell culture techniques. Cells were counted using a Neubaur counting chamber and diluted to $1.2 \times 10^7$ cells/mL in DMEM/F-12 supplemented 10% FBS. Cells (0.25 mL) and DNA (0.020 mL of 250 µg/mL) were gently mixed prior to electroporation. The mixture was then transferred to a 2 mm electroporation cuvette (BTX, San Diego, Calif.) and exposed to a 140 volt/1600µ Farad pulse. After electroporation, the cells were diluted in post-electroporation medium to a concentration of $1 \times 10^6$ cells/mL. Electroporated cells were then plated at $5 \times 10^5$ cells/well in 6-well plates (Becton-Dickinson, Lincoln Park, N.J.).

Example 4
Steady State Replication Cultures

Steady state HPV replication cultures were prepared by trypsinizing HPV transfected cells 48 hours post-electroporation and expanding them approximately 20-fold in large scale culture flasks. Transfected cells were concentrated to $6 \times 10^6$ cells/mL in basal medium supplemented with 5% DMSO and frozen at −150° C. Thawed cells were used directly under experimental conditions as described.

HPV-11-containing cell lines were derived by co-electroporation of HPV-11 DNA and pSV2neo. Forty-eight hours post-electroporation, cells were subjected to G418 (Life Technologies, Gaithersburg, Md.) selection for 10 days followed by release from selection. Individual G418 resistant colonies were isolated using cloning cylinders and expanded for molecular analysis.

Example 5
Hirt Extraction and DNA Digestion

Viral DNA was extracted according to the procedure of Hirt, *J. Mol. Biol.* 1967, 26, 365. Cells were incubated for 96 hours in culture with fresh medium (with or without drug) being applied at least every 48 hours. Cell monolayers were washed once with PBS prior to lysis, after which 1 mL of lysis buffer (10 mM Tris, pH 8.0, 1 mM EDTA, 0.5% SDS) was added to each well. Cell lysates were collected in 1.5 mL microcentrifuge tubes, adjusted to 1M NaCl, mixed gently and refrigerated for at least 4 hours. Samples were centrifuged at 10,000×g for 15 minutes. The supernatant of each sample was collected and extracted 2× with phenol/chloroform, 1× with chloroform and precipitated in ethanol with 0.2M NaCl. DNA samples were resuspended and digested overnight using 40 units HindIII and 60 units DpnI. Samples were precipitated in ethanol and resuspended in 30 $\mu$L of water.

Example 6
Southern Blot Analysis

Samples were electrophoresed through a 0.7% agarose gel, transferred to Amersham Hybond-H$^+$ in 1M ammonium acetate and crosslinked using the AutoLink setting on the Stratagene Stratalinker (Stratagene, San Diego, Calif.). The blots were rinsed in 2× SSC and pre-hybridized for 10 minutes at 68° C. in QuikHyb (Stratagene, San Diego, Calif.). High specific activity random primed probe was prepared using gel-purified unit length HPV-11, linearized pUC19 or a commercially available mix of HindIII digested lambda phage and HaeIII digested $\phi\chi$174 DNAs (Life Technologies, Gaithersburg, Md.). Target probe and molecular weight markers were present in hybridization reactions at $1\times10^6$ cpm/mL and $1\times10^5$ cpm/mL, respectively. No cross-hybridization between molecular weight probe and either HPV-11 or pUC19 was detected. After hybridization, the membranes were washed under stringent conditions, 60° C., 0.1× SSC and 0.1% SDS and quantitated by PhosphorImager (Molecular Dynamics, Sunnyvale, Calif.).

Example 7
Kinetics of HPV-11 DNA Replication

SCC-4 cells have been shown to support transient replication of HPV DNA, Del Vecchio et al., *J. Virol.* 1992, 66, 5949. SCC cells were electroporated with cloned HPV-11 DNA. Low molecular weight DNA was prepared by the method of Hirt, *J. Mol. Biol.* 1967, 26, 365. Methylated (input) DNA was digested with DpnI. DpnI-resistant DNA (replicated in cells) was linearized by HindIII. The DNAs were separated by electrophoresis and detected by Southern blotting using an HPV-11-specific probe under stringent hybridization conditions. A schematic representation of the introduction and analysis of HPV-11 DNA in SCC-4 cells is shown in FIG. 1.

DpnI-resistant unit length HPV-11 DNA was initially detected at 24 hours, and accumulated with time after electroporation. DpnI-sensitive viral DNA was gradually lost over the course of the experiment. Quantitation of the DpnI-resistant viral DNA band confirmed the accumulation of HPV-11 DNA. The accumulation of DpnI-resistant HPV-11 DNA was the result of viral replication and not simply demethylation of input DNA. This conclusion was supported by observations that neither the viral DNA (which had not been cleaved from its vector) nor pUC19 DNA resulted in the accumulation of DpnI-resistant DNAs. The results show that HPV-11 DNA is capable of autonomously replicating in SCC cells, and that this replication is dependent upon an intact viral genome.

Figure 2:
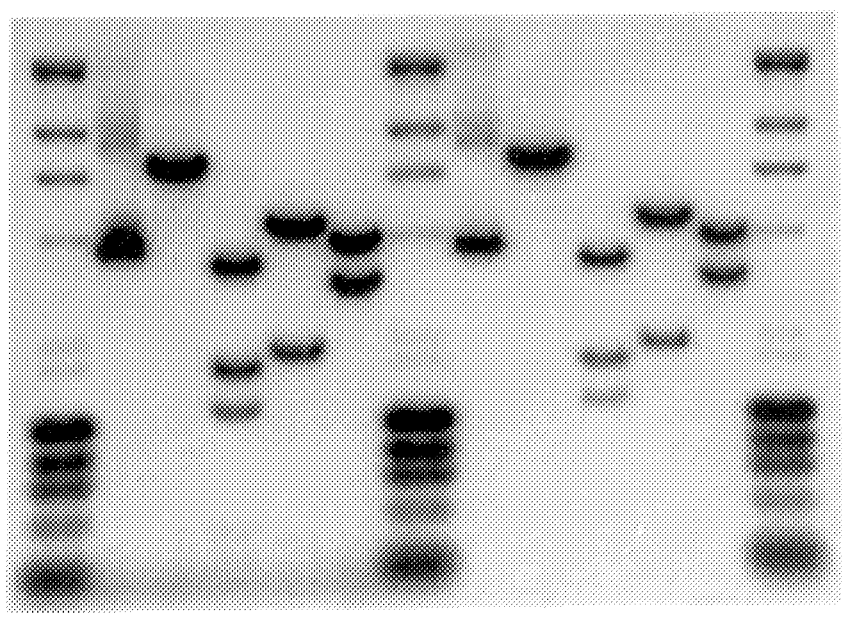
FIG. 2 is a Southern blot analysis of HPV DNA in transient and stable transfection experiments. DNA from either transient or stable transfection experiments was digested with a panel of restriction endonucleases and analyzed by Southern blotting.

Example 8
HPV-11 DNA Remains Episomal in Transient and Long Term Cultures In order to characterize the state of the viral genome, both transient and long term cultures, viral DNAs were prepared and analyzed by a panel of restriction endonucleases (FIG. 2). Digestion of DNA with XhoI, which does not cleave HPV-11 DNA, resulted in a single band with a mobility consistent with supercoiled DNA. Digestion with HindIII, which cuts HPV-11 DNA at a single site, resulted in a single band with a molecular weight of approximately 7.9 kilobases, consistent with full length HPV-11 DNA. Analysis with three multiple cut enzymes gave results consistent with full length episomal viral DNA with no detectable rearrangements or deletions.

Figure 3:
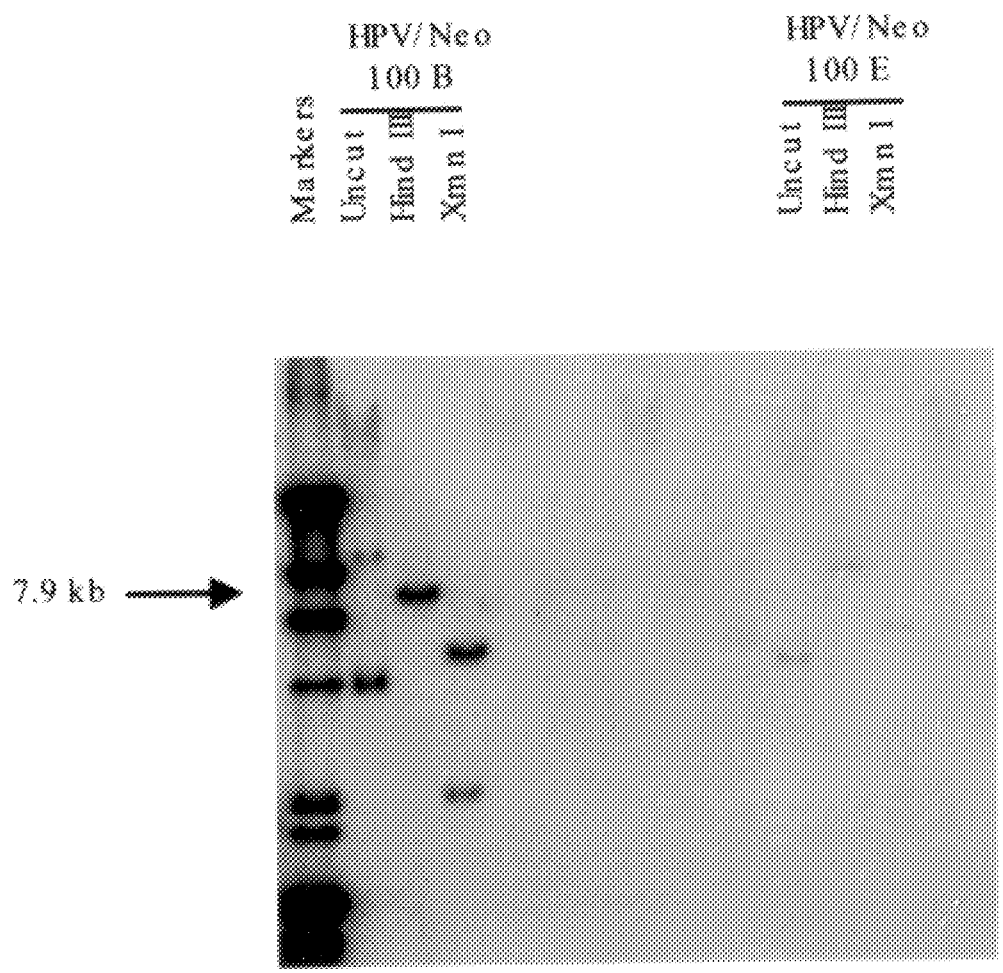
FIG. 3 shows the characterization of HPV DNA in G418 selected clones. Hirt DNA from G418-resistant colonies were digested with a panel of restriction endonucleases and analyzed by Southern blotting.

Analysis of G418-selected colonies showed that HPV-11 DNA remained episomal at six months post-electroporation (FIG. 3). Some clones maintained HPV-11 DNA at a relatively high copy number (30 to 40 copies/cell) while other clones maintained HPV-11 DNA at an extremely low copy number (1 to 2 copies/cell). It was observed that HPV-11 DNA-containing cell lines grew very slowly when compared to G418 selected cell lines derived from electroporation of pSV2neo alone or the non-transfected parental cell line. These results demonstrated that, upon electroporation, HPV-11 DNA establishes itself as an autonomously replicating plasmid, achieves a steady state level of plasmid, persists over several cell passages without selection, and withstands clonal selection.

Example 9
Inhibition of HPV-11 DNA Replication by Antisense Oligonucleotide and Other Antiviral Agents HPV-11 DNA and SCC-4 cells were mixed prior to electroporation according to Example 3. After electroporation, the SCC-4 cells were plated in a 96-well plate, incubated overnight, and then treated with drug for 4 hours. Seventy-two hours after drug treatment cells were harvested and analyzed for DpnI-resistant HPV-11 DNA.

Figure 4:
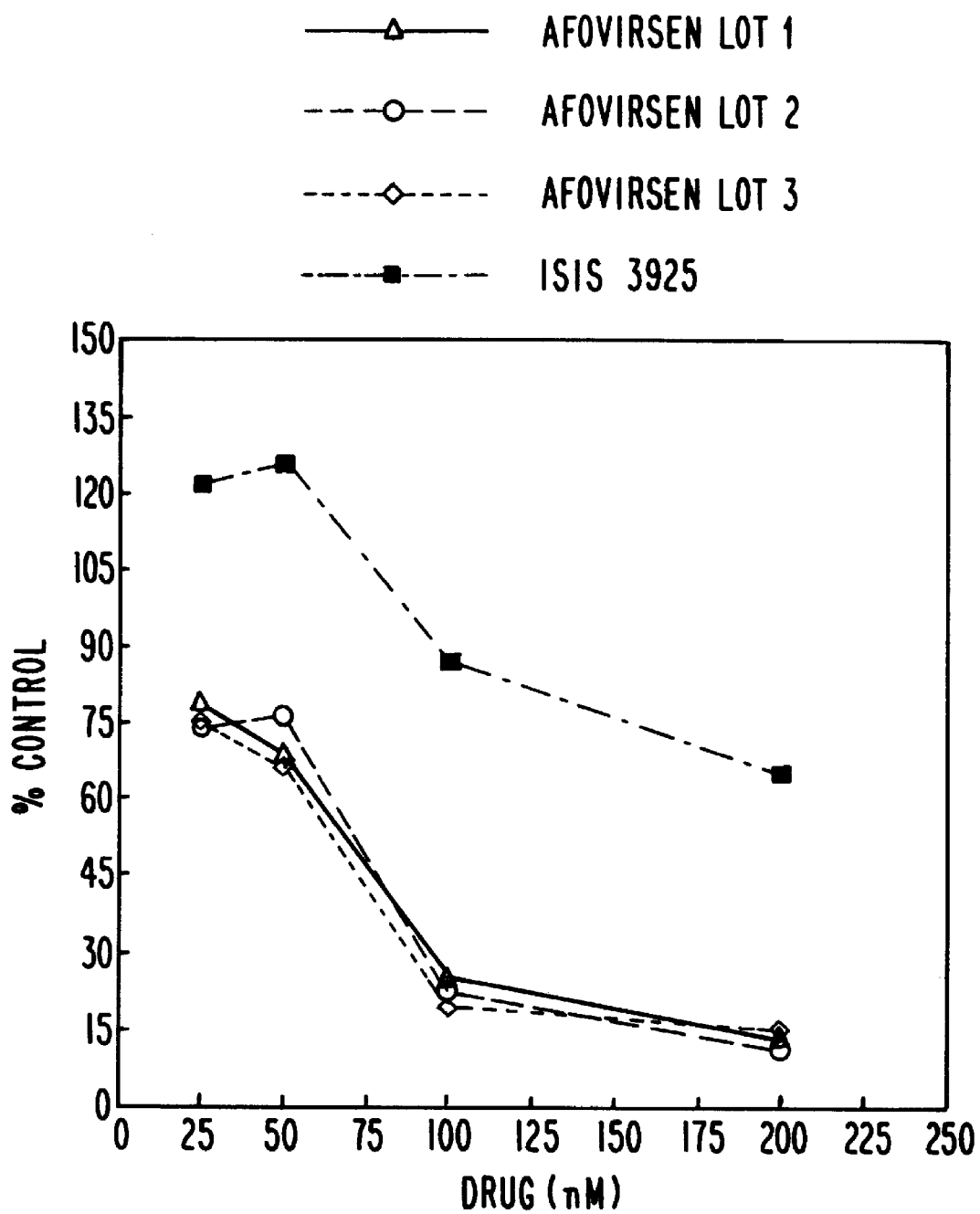
FIG. 4 is a graph of Afovirsen-mediated inhibition of HPV-11 DNA replication.

Afovirsen (ISIS 2105), a 20-mer phosphorothioate oligonucleotide, was designed to be complementary to the initiation codon of the E2 open reading frame of a region of conserved sequence between HPV-6 and HPV-11. Afovirsen was first identified as an oligonucleotide capable of inhibiting HPV-11 E2 transactivation, Cowsert et al., *Antimicrob. Agents Chemother.* 1993, 37, 171. When tested in this assay, Afovirsen (formulated in Lipofectin™) was able to inhibit replication of HPV-11 viral DNA in a dose- and sequence-dependent manner (FIG. 4). The apparent IC$_{50}$ of this inhibition was 70 nM.

5-FU and $\alpha$-interferon were evaluated for antiviral activity using this transient replication assay. 5-FU failed to inhibit HPV DNA replication in a dose-dependent manner with the only inhibitory dose simultaneously inducing significant toxicity. $\alpha$-Interferon induced a general reduction in HPV DNA replication, but failed to produce a dose response over a wide range of concentrations. 5-FU demonstrated 24% inhibition of cell growth at a concentration of 0.1 $\mu$M and $\alpha$-interferon exhibited 67% inhibition of cell growth at an increased concentration of 190 $\mu$M, while Afovirsen inhibited cell growth to the extent of 77% at a concentration of 0.1 $\mu$M.

Other antiviral agents such as ribavirin, acyclovir and ganciclovir failed to show convincing antiviral activity in the assay of the present invention. Ribavirin, acyclovir and ganciclovir failed to inhibit HPV-11 DNA replication at subtoxic doses, and exhibited 0% to 36% inhibition of cell growth at a concentration of 0.1 $\mu$M.

Sodium butyrate and bromodeoxyuridine (BdrU) were found to have significant antiviral activity in this assay. Sodium butyrate stimulated HPV-11 DNA replication at low doses. However, it was a potent inhibitor of HPV-11 DNA replication at subtoxic doses with an approximate $IC_{50}$ of 5 $\mu$M. BdrU also exhibited potent antiviral activity in this assay with an approximate $IC_{50}$ of 10 $\mu$M.

What is claimed:

1. A method of screening a candidate drug for antiviral activity against HPV comprising the steps of:
    (a) providing a cell culture comprising growing cells containing intact HPV genome capable of undergoing replication;
    (b) dividing said cell culture into a first portion and a second portion of said cells;
    (c) adding said candidate drug to said first portion of said cells;
    (d) incubating said first portion and said second portion for a sufficient time to allow measurable growth of said cells;
    (e) determining the amount of HPV DNA which has accumulated due to replication in said first portion and said second portion of said cells; and
    (f) comparing the amount of said HPV DNA which has accumulated due to replication in said first portion and said second portion of said cells, wherein an increase in the amount of said HPV DNA which has accumulated due to replication in said second portion compared to said first portion of said cells indicates that said candidate drug possesses antiviral activity.

2. The method of claim 1 wherein the amount of HPV DNA which has accumulated due to replication in said cells is determined by digestion with DpnI, with an increase in the amount of DpnI-resistant DNA accumulating in said second portion of said cells compared to said first portion of said cells being indicative of antiviral activity.

3. The method of claim 1 wherein said papillomavirus is HPV-11.

* * * * *

UNITED STATES PATENT AND TRADEMARK OFFICE
CERTIFICATE OF CORRECTION

PATENT NO. : 5,821,050
DATED : October 13, 1998
INVENTOR(S) : Cowsert, et al.

It is certified that error appears in the above-indentified patent and that said Letters Patent is hereby corrected as shown below:

At col 4, line 25, please delete "PUC19" and insert therefor --pUC19--.

Signed and Sealed this

Second Day of March, 1999

Attest:

Q. TODD DICKINSON

*Attesting Officer*     *Acting Commissioner of Patents and Trademarks*